United States Patent
De Wit et al.

(10) Patent No.: US 6,835,834 B2
(45) Date of Patent: Dec. 28, 2004

(54) PROCESS FOR PREPARING MELAMINE FROM UREA

(75) Inventors: Nora Anna De Wit, Masstricht (NL); Rob Kasimier Gulpers, Landgraaf (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/210,877

(22) Filed: Aug. 2, 2002

(65) Prior Publication Data

US 2003/0050473 A1 Mar. 13, 2003

Related U.S. Application Data

(63) Continuation of application No. PCT/NL01/00046, filed on Jan. 23, 2001.

(30) Foreign Application Priority Data

Feb. 3, 2000 (NL) .............................................. 1014281

(51) Int. Cl.$^7$ ...................... C07D 251/60; C07D 251/62

(52) U.S. Cl. ........................................ 544/201; 544/203
(58) Field of Search ................................. 544/201, 203

(56) References Cited

FOREIGN PATENT DOCUMENTS

| EP | 114442 | 8/1984 |
|---|---|---|
| WO | 96 20933 | 7/1996 |

OTHER PUBLICATIONS

"The manufacture of non–fertilizer nitrogen products", NITROGEN, vol. 139, Sep. 1982, pp. 32–39.

*Primary Examiner*—Richard L. Raymond
*Assistant Examiner*—Venkataraman Balasubramanian
(74) *Attorney, Agent, or Firm*—Mayer, Brown, Rowe & Maw LLP

(57) ABSTRACT

Process for preparing melamine from urea at elevated temperature and in the presence of a catalyst, in which a gaseous product stream is obtained which is contacted with a liquid coolant in a cooling zone and in which a proportion of the concentrated aqueous carbamate solution from the absorption zone is returned to the cooling zone.

7 Claims, No Drawings

PROCESS FOR PREPARING MELAMINE FROM UREA

CROSS REFERENCE TO RELATED APPLICATION

This application is a continuation of International Application No. PCT/NL01/00046, filed Jan. 23, 2001, the disclosure of which is incorporated herein by reference thereto.

The invention relates to a process for preparing melamine from urea at elevated temperature and in the presence of a catalyst, in which a gaseous product stream is obtained which is contacted with a liquid coolant in a cooling zone.

A similar process is disclosed in for example WO-96/20933. This describes the preparation of melamine by supplying urea and ammonia to a reactor at a pressure of between 1.4 MPa and 2.0 MPa and a temperature high enough for virtually complete conversion of urea into melamine in the presence of a catalyst. In the process there is obtained a gas stream containing melamine, ammonia and carbon dioxide. In WO-96/20933 this gas stream is cooled with an aqueous coolant in what is known as a quench pipe with evolution of a vapour-liquid mixture, which mixture is virtually free from solid constituents. This vapour-liquid mixture is separated in this quench pipe into an aqueous melamine product stream and a vapour stream. The vapour stream from the quench pipe is virtually free from urea and melamine and consists essentially of ammonia, carbon dioxide and water vapour. The aqueous melamine product stream is virtually free from solids and contains dissolved ammonia and carbon dioxide. After the dissolved ammonia and carbon dioxide are removed with the aid of steam in a stripping section, the aqueous melamine product stream is passed to the melamine purification where the melamine is recovered. In this stripping section evolves also a vapour stream consisting essentially of ammonia, carbon dioxide and water vapour. The vapour stream from the quench pipe, together with the vapour stream from the stripping section, is scrubbed in a scrubbing section with an aqueous solution (mother liquor) from the melamine purification in order to remove melamine residues still present in the vapour stream. This aqueous solution may contain ammonia, carbon dioxide and melamine. The quench pipe and scrubbing section make up the cooling zone in the process according to WO-96/20933. Next, the gas stream from the scrubbing section is passed to an absorption zone where it is contacted with an aqueous ammonia stream from the melamine purification and liquid ammonia, in which process there is obtained a solution of concentrated aqueous ammonia and carbon dioxide (carbamate solution) and ammonia vapour virtually free from water and carbon dioxide. In WO-96/20933, this ammonia vapour is condensed and partly returned to the absorption zone, the remainder after evaporation being used as fluidization gas for the reactor. The aqueous solution from the scrubbing section is passed to the quench pipe and used as coolant there.

The concentrated aqueous carbamate solution from the absorption zone, which WO-96/20933 reports contains 20–35% by weight of water, is for example supplied to a urea plant. Thus, in WO-96/20933 the gas mixture coming from the reactor is cooled with the mother liquor from the melamine purification, which liquor is passed to the quench pipe via the scrubbing section.

WO-96/20933 states that the water content of the carbamate solution from the absorption zone is so low, i.e. 20–35% by weight, that a concentration step, in which water is removed from the carbamate solution, is not needed before the carbamate solution is supplied to a urea plant.

Experiments carried out by the applicant in accordance with the process described in WO-96/20933 indicate, however, that it is advantageous to remove water from the carbamate solution if the aim is to operate the combination of melamine plant and urea plant in the most economical manner.

In a melamine plant water is used among others as a component of the liquid coolant. A proportion of the water eventually ends up in the carbamate solution from the absorption zone which is supplied to for example a urea plant.

Experiments and calculations by the applicant indicate that in the process according to WO-96/20933 the amount of water in the carbamate stream discharged to the urea plant is about 2.5 tons of water per ton of melamine. In an economically optimum process, such as the Stamicarbon process described in Nitrogen No. 139, September/October 1982, pp. 32–39, in which the excess water is removed in a concentration step, the amount of water in the carbamate solution supplied to a urea plant is about 0.5–1.0 ton of water per ton of melamine. In the Stamicarbon process the gas mixture coming from the melamine reactor is cooled with a liquid coolant in the quench columns. The mixture of vapour, liquid and, possibly, solid matter, is separated in the quench columns into a vapour phase and a liquid phase. The vapour phase is passed to an absorption zone and the liquid phase to the melamine recovery.

The aforementioned tons of water per ton of melamine may be converted to a water concentration in the carbamate solution from the absorption zone, if the $NH_3/CO_2$ ratio of the carbamate solution exported is determined. If the plant according to WO-96/20933 is operated in an economically optimum manner, this ratio is minimum, for example 1.3 kg of $NH_3$ per kg of $CO_2$. This means that the water concentration in the carbamate solution from the absorption zone in the process according to WO-96/20933 is 45–50% by weight. In the aforementioned Stamicarbon process this is 20–25% by weight.

For supplying this 45–50% by weight of water-containing carbamate stream to a urea plant it is economically attractive to further concentrate the carbamate solution by removing water from this solution. The drawback hereof is that this entails additional investments and that the process becomes more costly due to increased usage of steam, cooling water and electricity.

It has been found that this drawback can be overcome by returning a proportion of the concentrated aqueous carbamate solution from the absorption zone to the cooling zone. In particular, a proportion of the concentrated aqueous carbamate solution from the bottom of the absorption zone is returned to the cooling zone.

In WO-96/20933, this cooling zone is made up of the quench pipe and the scrubbing section; in the Stamicarbon process this cooling zone consists of the quench columns. In both processes, the remainder of the concentrated aqueous carbamate solution from the absorption zone is supplied to for example a urea plant, preferably a high-pressure section of a urea plant, without any further processing.

In an embodiment of the invention the gas stream coming from the quench columns or the scrubbing section is cooled in a condenser ahead of the absorption zone. Here, the gas stream is cooled by at least 5° C., preferably at least 10° C. and in particular at least 15° C. The dilute carbamate solution coming from the condenser ahead of the absorption zone is passed to the cooling zone. In this condenser evolves a gas which is enriched with ammonia and carbon dioxide and which is passed to the absorption zone. In the absorption zone then evolves a concentrated aqueous carbamate solution which contains less water and which is partly returned to the cooling zone.

The liquid coolant preferably consists of an aqueous carbamate solution composed of a proportion of the concentrated aqueous carbamate solution from the absorption zone to which mother liquor from the melamine purification (backend section) may be added, and ammonia, carbon dioxide and water condensed in the cooling zone.

20–40% by weight of the gas going to the absorption zone is returned in condensed form to the cooling zone. In the specific case where the bottom product from the absorption zone is returned, this means that 30–70% by weight of the concentrated carbamate solution from the absorption zone is used for cooling the gas stream coming from the reactor and preferably 35–65% by weight. The remainder is supplied to for example a urea plant but may also be used for other purposes such as a fertilizer plant or production of ammonia.

It has been found that in the process of the invention the water content of the concentrated carbamate solution from the absorption zone eventually amounts to 20–35% by weight. This does render the proportion of this carbamate solution which is returned to a urea plant suitable for direct processing. This means that the concentration step is superfluous.

Furthermore, it was found that the process of the invention is particularly suitable for so-called gas-phase melamine plants operating at a pressure of 0.6–2.5 MPa, more particularly at pressures of between 0.7 MPa and 2.2 MPa.

The process of the present invention is particularly suitable for modifying existing melamine processes such as those described in WO-96/20933 and the Stamicarbon process as described in the aforementioned Nitrogen publication.

The invention is illustrated by the following examples.

EXAMPLES I–III

Melamine was prepared in a cylindrical fluidized bed with an inside diameter of 1 metre and a height of 15 m. The catalyst was fluidized by introducing ammonia through a gas distribution plate and was heated by heat exchanger tubes in the reactor through which molten salt flowed. Liquid urea was sprayed into the reactor with the aid of a two-phase sprayer using ammonia as atomizing gas. The reactor was operated at 390° C. and a total pressure of 0.7 MPa (Example I), 1.7 MPa (Example II) and 2.0 MPa (Example III). Urea was metered at the rate of 1.4 tons/hour with 0.7 ton of ammonia per hour via the two-phase sprayers. Ammonia was supplied through the fluidization plate at the rate of 0.7 ton/hour. The conversion of water-free urea to melamine relative to equilibrium was higher than 98%. The gas stream from the reactor contained $NH_3$, $CO_2$, melamine vapour and traces of by-products and was cooled in the cooling zone with liquid coolant. A proportion of the concentrated aqueous carbamate solution from the absorption zone was returned to the cooling zone. The remainder of the concentrated carbamate solution was supplied to the adjacent urea plant. The proportion of the carbamate from the absorption zone that was returned to the cooling zone and the amount of water in the carbamate stream from the absorption zone are stated in Table 1.

Comparative Example A

Analogously to Examples I–III, melamine was prepared except that no carbamate from the absorption zone was returned to the cooling zone. The carbamate stream coming from the absorption zone was then too dilute for it to be supplied to a urea plant without an intermediate step. Refer to Table 1.

TABLE 1

|  | Example | | | |
| --- | --- | --- | --- | --- |
|  | I | II | III | A |
| Pressure in Mpa | 0.7 | 1.7 | 2.0 | 1.7 |
| Proportion of carbamate from absorption zone returned to cooling zone in % by weight | 56 | 51 | 50 | 0 |
| Water content of carbamate from absorption zone in % by weight | 28 | 25 | 24 | 49 |
| Amount of exported water in kg per kg of melamine | 0.89 | 0.74 | 0.70 | 2.5 |

What is claimed is:

1. Process for preparing melamine from urea at elevated temperature and in the presence of a catalyst, in which a gaseous product stream is obtained which is contacted with a liquid coolant in a cooling zone and forms a vapor comprising ammonia and carbon dioxide, and wherein the vapor is absorbed in an absorption zone to form a concentrated aqueous carbamate solution, wherein a proportion of the concentrated aqueous carbamate solution from the absorption zone is returned to the cooling zone.

2. Process according to claim 1, wherein the gaseous product stream coming from the reactor is cooled with a proportion of the carbamate solution from the absorption zone, to which solution mother liquor from the melamine purification and ammonia, carbon dioxide and water condensed in the cooling zone may be added.

3. Process according to claim 1, wherein 30–70% by weight of the concentrated aqueous ammonium carbamate stream from the bottom of the absorption zone is used for cooling the gas stream coming from the reactor.

4. Process according to claim 1, wherein the gas stream coming from quench columns or scrubbing section downstream of the melamine reactor is cooled in a condenser ahead of the absorption zone.

5. Process according to claim 1, wherein the gas coming from the melamine reactor has a pressure of between 0.6 and 2.5 MPa.

6. Process according to claim 5, wherein the gas coming from the melamine reactor has a pressure of between 0.7 and 2.2 MPa.

7. A method for modifying an existing melamine plant comprising applying the process according to claim 1.

* * * * *